(12) United States Patent
Higuchi

(10) Patent No.: US 12,090,228 B2
(45) Date of Patent: Sep. 17, 2024

(54) PACKAGE AND METHOD FOR PRODUCING THE SAME

(71) Applicant: SEIKAGAKU CORPORATION, Tokyo (JP)

(72) Inventor: Mine Higuchi, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 960 days.

(21) Appl. No.: 16/975,252

(22) PCT Filed: Feb. 27, 2019

(86) PCT No.: PCT/JP2019/007447
§ 371 (c)(1),
(2) Date: Aug. 24, 2020

(87) PCT Pub. No.: WO2019/167991
PCT Pub. Date: Sep. 6, 2019

(65) Prior Publication Data
US 2020/0397703 A1     Dec. 24, 2020

(30) Foreign Application Priority Data

Feb. 28, 2018 (JP) ................. 2018-035884
Jul. 27, 2018 (JP) ................. 2018-141542

(51) Int. Cl.
A61K 9/19     (2006.01)
A61K 38/51    (2006.01)

(52) U.S. Cl.
CPC ............. *A61K 9/19* (2013.01); *A61K 38/51* (2013.01); *C12Y 402/02004* (2013.01)

(58) Field of Classification Search
CPC ... A61K 9/19; A61K 38/51; C12Y 402/02004
See application file for complete search history.

(56) References Cited

U.S. PATENT DOCUMENTS

| 5,496,718 A | 3/1996 | Hashimoto et al. |
| 6,007,810 A | 12/1999 | Ishikawa et al. |
| 2006/0160720 A1 | 7/2006 | Jensen et al. |
| 2010/0168011 A1 | 7/2010 | Jennings, Jr. et al. |
| 2013/0266555 A1 | 10/2013 | Sirogane et al. |
| 2015/0136723 A1 | 5/2015 | Bamba et al. |
| 2016/0158324 A1 | 6/2016 | Zhu et al. |

FOREIGN PATENT DOCUMENTS

| EP | 0 875 253 A2 | 11/1998 |
| EP | 3760219 A1 | 1/2021 |
| JP | 6 135851 A | 5/1994 |
| JP | 6 153947 A | 6/1994 |
| JP | 7 67642 A | 3/1995 |
| JP | 11 236336 A | 8/1999 |
| JP | 3140797 B2 | 12/2000 |
| JP | 2008 50320 A | 3/2008 |
| JP | 2010 512399 A | 4/2010 |
| WO | 01/17567 A2 | 3/2001 |
| WO | 2005 046699 A1 | 5/2005 |
| WO | 2012/081227 A1 | 6/2012 |
| WO | 2013 179514 A1 | 12/2013 |

OTHER PUBLICATIONS

Extended European Search Report issued for European application No. 19760698.1 dated Dec. 16, 2021.
International Search Report issued in International Patent Application No. PCT/JP2019/007447, dated Apr. 9, 2019 and English Translation thereof.
International Preliminary Report of Patentability issued in International Patent Application No. PCT/JP2019/007447, dated Sep. 24, 2020, and English Translation thereof.
Ives J A et al., "Enzyme stabilization by glass-derived silicates in glass-exposed aqueous solutions," *Homeopathy*, Churchill Livingstone, Amsterdam, NL, vol. 99, No. 1, Jan. 1, 2010, pp. 15-24, XP026850487, ISSN: 1475-4916 [retrieved on Jan. 15, 2010].
Robert Hormes, "Highly chemically inert pharmaceutical vials SCHOTT Type I plus ®," PDA Journal of GMP and Validation in Japan, vol. 7, No. 1 (2005), pp. 16-20, with English translation.
SCHOTT Type I plus ® Vials, product sheet, Jun. 2017.

*Primary Examiner* — Bong-Sook Baek
*Assistant Examiner* — Ayaan A Alam
(74) *Attorney, Agent, or Firm* — GREENBLUM & BERNSTEIN, P.L.C.

(57) ABSTRACT

There is provided a package wherein a pharmaceutical composition containing a saccharide-degrading enzyme is contained in a container, whereby reduction in titer caused by a low amount of enzyme is suppressed. A package comprising a pharmaceutical composition and a container, wherein the pharmaceutical composition is a lyophilized preparation containing a saccharide-degrading enzyme as an active ingredient, and the container contains the pharmaceutical composition, the inner surface of the container comprising at least one material selected from the group consisting of fine ceramics, silicone resins and fluorine resins.

15 Claims, No Drawings

PACKAGE AND METHOD FOR PRODUCING THE SAME

TECHNICAL FIELD

The present invention relates to a package comprising a pharmaceutical composition containing an enzyme as an active ingredient which is put into a container and to a method for producing the same.

BACKGROUND ART

Pharmaceutical compositions that comprise saccharide-degrading enzymes as active ingredients are used in various disease fields. For example, pharmaceutical compositions for treatment of lysosomal disease such as Aldurazyme®, Elaprase®, Naglazyme®, Replagal® and Vimizim®, wherein the active ingredients are saccharide-degrading enzymes at about 3 mg/vial to about 10 mg/vial, are marketed as liquid preparations for injection. Also, International Publication No. WO 2012/081227, for example, describes a therapeutic agent for disc herniation containing a saccharide-degrading enzyme (particularly chondroitinase ABC) as the active ingredient.

SUMMARY OF INVENTION

Lyophilized preparations are superior to liquid preparations from the viewpoint of reducing distribution cost. On the other hand, titers of enzyme are often reduced due to lyophilization, and therefore modifications have been introduced in production of lyophilized preparations so as to allow products with the desired enzyme activity to be obtained. For example, the Examples of International Publication No. WO 2012/081227 describe an example in which, considering the reduction in titer resulting from lyophilization of a small amount of enzyme, a lyophilized preparation is obtained after the enzyme solution prepared in a large excess of the unit dose as the amount necessary for a single dose, has been put into a container. As described in this publication, once the obtained lyophilized preparation has been dissolved and diluted, it is separated off in the necessary amount to prepare a dosing solution containing the active component in an amount necessary for a single dose.

In a method wherein an enzyme solution in an amount exceeding the unit dose is prepared first and then a portion is separated off as a single dose, the remaining enzyme that is not used for administration is discarded. So, the remaining expensive enzyme is wasted in some cases. In addition, since a procedure is required for separation of the small amount from the prepared enzyme solution, it is also necessary to be mindful of loss of activity during the procedure.

The present inventors have found that the reduction in titer that occurs during production of a package that contains a lyophilized preparation is unexpectedly increased if the amount of saccharide-degrading enzyme contained in is small. The present inventors further found that this reduction in titer is especially notable when the amount of saccharide-degrading enzyme contained in is at a lower level than a conventional pharmaceutical composition.

It is therefore an object of the present invention to provide a package comprising a pharmaceutical composition containing a saccharide-degrading enzyme as an active ingredient, contained in a container, which suppresses the reduction in titer that occurs when the amount of saccharide-degrading enzyme contained in is small.

One aspect of the present invention relates to a package comprising a pharmaceutical composition and a container, wherein the pharmaceutical composition is a lyophilized preparation comprising a saccharide-degrading enzyme as an active ingredient, the container contains the pharmaceutical composition and has at least one material selected from the group consisting of fine ceramics, silicone resins and fluorine resins at the inner surface of the container.

Another aspect of the present invention relates to a method for producing a package comprising a pharmaceutical composition and a container containing the pharmaceutical composition, the method comprising a step of putting a solution comprising a saccharide-degrading enzyme into the container having at least one material selected from the group consisting of fine ceramics, silicone resins and fluorine resins on its inner surface, and a step of lyophilizing the solution to obtain the pharmaceutical composition.

DESCRIPTION OF EMBODIMENTS

According to one aspect of the present invention, it is possible to provide a package comprising a saccharide-degrading enzyme-containing pharmaceutical composition contained in a container, wherein the reduction in titer caused by a low amount of saccharide-degrading enzyme being contained in is suppressed.

The present invention will now be described in detail, with the understanding that the present invention is not limited by the embodiments described. As used herein, the term "step" refers not only to an independent step, but also includes any step that cannot be clearly distinguished from other steps, if the initial purpose of the step is achieved. When multiple substances corresponding to each component are present in the composition, the content of each component in the composition means the total of the multiple substances in the composition, unless otherwise specified.

(1) Pharmaceutical Composition and Package

The pharmaceutical composition is a lyophilized preparation containing a saccharide-degrading enzyme as an active ingredient. The pharmaceutical composition may be a unit dose formulation. As used herein, "unit dose" means the necessary amount prepared for a single administration, a unit dose formulation being formulated with the pharmaceutical composition in the unit dose. The unit dose may include an added amount necessary for preparation of a single dosing solution, in addition to the effective dose.

The package includes at least a container and the pharmaceutical composition contained in the container.

The "saccharide-degrading enzyme" is not particularly limited, as long as it is one that can be used as a drug. Examples of saccharide-degrading enzymes can include, for example, glycosaminoglycan degrading enzymes; glycosidase; peptides: N-glycanase (PNGaseF, endoglycosidase H, etc.), α-L-iduronidase, α-galactosidase, β-galactosidase, β-glucuronidase, β-glucocerebrosidase, idursulfase, iduronate-2-sulfatase, N-acetylgalactosamine-6-sulfatase, N-acetylgalactosamine-4-sulfatase, etc. Examples of glycosaminoglycan degrading enzymes include, for example, keratanases such as keratanase I and keratanase II; heparinases such as heparinase I, heparinase II and heparinase III; heparitinases such as heparitinase IV, heparitinase V, heparitinase T-I, heparitinase T-II, heparitinase T-III and heparitinase T-IV; chondroitinases such as chondroitinase ABC, chondroitinase ACI, chondroitinase ACII, chondroitinase ACIII, chondroitinase B and chondroitinase C; hyaluronidases such as hyaluronidase derived from Actinomycetes and hyaluronidase derived from *Streptococcus*, etc. Examples of glycosidases include, for example, microbial β-galactosidase, α-galactosidase, etc.

In one embodiment, a glycosaminoglycan degrading enzyme is used as the saccharide-degrading enzyme. Glycosaminoglycan degrading enzymes include hyaluronidases, chondroitinases, heparinases, keratanases, heparanases, heparitinases, etc. Chondroitinases are preferred saccharide-degrading enzymes, among which chondroitinase ABC, chondroitinase B, chondroitinase ACI and chondroitinase ACII are more preferred, and chondroitinase ABC (also known as Condoliase) is especially preferred. Chondroitinase ABC is an enzyme that degrades hyaluronic acid, chondroitin sulfate, chondroitin, dermatan sulfate, etc., into disaccharides or oligosaccharides that include unsaturated sugars.

There are no particular restrictions on the source of the saccharide-degrading enzyme. In one preferred embodiment, a microbial saccharide-degrading enzyme is used. For example, non-restrictive examples of microbes include those belonging to *Bacillus, Escherichia, Pseudomonas, Flavobacterium, Proteus, Arthrobacter, Streptococcus, Bacteroides, Aspergillus, Elizabethkingia, Streptomyces*, etc. When the saccharide-degrading enzyme is chondroitinase ABC, for example, an example can be one derived from *Proteus vulgaris* (for example, *Proteus vulgaris* chondroitinase ABC).

The method for producing the saccharide-degrading enzyme, etc., is not particularly restricted. An exemplary method for producing the saccharide-degrading enzyme includes a step of obtaining a culture of microbes or animal cells that produce the saccharide-degrading enzyme, and a step of collecting the saccharide-degrading enzyme from the cultured product.

The saccharide-degrading enzyme produced by the microbes may be the original product of the microbes, or it may be obtained after modifying the microbes by a genetic engineering method, etc., as described below, so as to produce the target enzyme. For example, when the saccharide-degrading enzyme is chondroitinase ABC, it may be produced by culturing a microbe such as *Proteus vulgaris*, or it may be produced by a genetic engineering method using DNA coding for the chondroitinase ABC, etc. The saccharide-degrading enzyme may have the same amino acid sequence as the original product of the organism, but alternatively it may have a deletion, substitution and/or addition, etc., of some of the amino acids, as long as the intended object of the drug is still achieved.

Examples of microbes can include, for example, microbes belonging to *Bacillus, Escherichia, Pseudomonas, Flavobacterium, Proteus, Arthrobacter, Streptococcus, Bacteroides, Aspergillus, Elizabethkingia* and *Streptomyces*. The growth conditions (for example, culture medium, culturing conditions, etc.) for the microbe can be set as desired by a person skilled in the art, being appropriately selected according to the microbe used. By using a microbe to produce the saccharide-degrading enzyme, it is possible to produce larger amounts at lower cost than by production of the saccharide-degrading enzyme using animal cells.

The method for producing the saccharide-degrading enzyme may include a step of introducing a recombinant vector that expresses a gene coding for the target saccharide-degrading enzyme, into a host. The vector used can be, for example, a suitable expression vector (for example, phage vector, plasmid vector or the like) (preferably including a regulatory sequence such as a promoter), that is able to express the introduced gene. The vector is selected as appropriate for the host cells. More specifically, examples of these host-vector systems include combinations of *Escherichia coli* (*E. coli*) with prokaryotic cell expression vectors such as the pET Series, pTrcHis, pGEX, pTrc99, pKK233-2, pEZZ18, pBAD, pRSET and pSE420; or combinations of mammalian cells such as COS-7 cells or HEK293 cells with mammalian cell expression vectors such as the pCMV Series, pME18S Series or pSVL; as well as insect cells, yeast and *Bacillus subtilis* host cells, etc., and their various corresponding vectors.

Also, as above-described vectors, it is possible to use the vectors that are constructed so as to express fusion proteins of the proteins encoded by the transferred genes, with marker peptides, signal peptides, etc. Examples of such peptides include, for example, Protein A, the insulin signal sequence, His-tag, FLAG, CBP (calmodulin-binding protein), GST (glutathione-S-transferase), etc. Regardless of the vector used, a common method may be used for treatment with restriction enzymes, etc., that allow subsequent linkage of the nucleic acid sequence insert and vector, the linkage being after blunting, with sticky ends, etc., as necessary.

Transformation of the host with the vector can be carried out by a common method. For example, the vector can be introduced into the host for transformation, by a method using a commercially available transfection reagent, or by a DEAE-dextran method, electroporation method, or a method using a gene gun, etc.

The growth conditions (for example, culture medium, culturing conditions, etc.) for the microbes, animal cells or the like that produce the saccharide-degrading enzyme are selected as appropriate for the microbes or cells used. In the case of where *E. coli* is used, for example, a culture medium appropriately prepared with LB medium, etc., as the main component can be used. Also, for example, when COS-7 cells are used as the host cells, DMEM medium containing about 2% (v/v) fetal bovine serum can be used for culturing under a condition of 37° C.

The saccharide-degrading enzyme can be collected from the growth product by known methods for extraction and purification of proteins, depending on the form of the saccharide-degrading enzyme that is produced. For example, when the saccharide-degrading enzyme is produced in soluble form secreted in the medium (the culture supernatant), the medium may be harvested and used directly as the saccharide-degrading enzyme. When the saccharide-degrading enzyme is produced in soluble form secreted into the cytoplasm, or in an insoluble (membrane-bound) form, it can be extracted by a treatment procedure such as extraction by cell disruption, such as a method using a nitrogen cavitation device, homogenization, a glass bead mill method, sonication, an osmotic shock method or a freezing-thawing method, or surfactant extraction, or a combination of these methods. The saccharide-degrading enzyme may also be purified by conventional and publicly known processes of the prior art such as salting out, ammonium sulfate fractionation, centrifugal separation, dialysis, ultrafiltration, adsorption chromatography, ion-exchange chromatography, hydrophobic chromatography, reversed-phase chromatography, gel permeation chromatography, affinity chromatography or electrophoresis, and a combination of these processes, etc.

The saccharide-degrading enzyme may be used alone or as a combination of two or more different types. The saccharide-degrading enzyme may also have addition of chemically modified groups that are publicly known in the prior art, such as by acetylation, polyalkylene glycolation (for example, polyethylene glycolation), alkylation, acylation, biotinylation, labeling (for example, labeling with a fluorescent substance, a luminescent substance, etc.), phosphorylation or sulfation.

The pharmaceutical composition may include a pharmaceutically acceptable carrier. As used herein, a "pharmaceutically acceptable carrier" is typically a component normally used in drugs, such as a commonly used excipient, binder, buffering agent, water for injection, tonicity agent, preservative or soothing agent.

Examples of buffering agents include, for example, buffering agents containing one or more selected from the group consisting of hydrochloric acid, sodium hydroxide, sodium carbonate, sodium hydrogencarbonate, phosphoric acid, potassium dihydrogenphosphate, dipotassium hydrogenphosphate, sodium dihydrogenphosphate, disodium hydrogenphosphate, aminoacetic acid, sodium benzoate, citric acid, sodium citrate, acetic acid, sodium acetate, tartaric acid, sodium tartrate, lactic acid, sodium lactate, ethanolamine, arginine, ethylenediamine, etc., among which at least one of sodium dihydrogenphosphate and disodium hydrogenphosphate being preferred.

Examples of tonicity agents include sodium chloride, potassium chloride, glycerin, mannitol, sorbitol, boric acid, borax, glucose, propylene glycol, etc.

For example, specific examples of other pharmaceutically acceptable carriers include dextrans, sucrose, lactose, maltose, xylose, trehalose, mannitol, xylitol, sorbitol, inositol, serum albumin, gelatin, creatinine, polyalkylene glycol, nonionic surfactants (for example, polyoxyethylene sorbitan fatty acid ester, polyoxyethylene hydrogenated castor oil, sucrose fatty acid ester and polyoxyethylene-polyoxypropylene glycol), etc., among which at least one of sucrose and polyalkylene glycol are preferred, and at least one of sucrose and polyethylene glycol are more preferred. Polyethylene glycol preferably has an average molecular weight of not less than 200 and not more than 25000, and more preferably it is a solid at ordinary temperature, for example, with an average molecular weight of not less than 2000 and not more than 9000, and even more preferably not less than 3000 and not more than 4000. Examples of polyethylene glycol can include, for example, polyethylene glycol with an average molecular weight of 3250, 3350 and 4000. When a mixture of polyethylene glycol and sucrose is used as the pharmaceutically acceptable carrier, they are preferably mixed such that the weight ratio of polyethylene glycol/sucrose is usually in the range of 1/10 to 10/1, and more preferably such that the weight ratio of polyethylene glycol/sucrose is about 2/1.

As used herein, the "container" is not particularly restricted as long as it is able to contain the pharmaceutical composition. Examples of containers include syringes, vials, ampules, injectors, etc., with vials being preferred. The base material of the container can be glass, plastic, etc., for example, with glass being preferred. Glass includes borosilicate glass, soda lime glass, etc., for example. The container preferably also has a stopper member or cap, and more preferably it has a rubber stopper. There are no particular restrictions on the size of the container, which may be not less than 0.5 mL and not more than 100 mL, for example, preferably not less than 1 mL and not more than 10 mL, more preferably not less than 2 mL and not more than 4 mL, and even more preferably 3 mL. The package comprising the pharmaceutical composition contained in the container may encapsulate an inert gas such as nitrogen gas or argon gas, or it may be deaerated.

The container may comprise at least one material selected from the group consisting of fine ceramics, silicone resins and fluorine resins on its inner surface. Examples of fine ceramics include, for example, a metal oxide, a metal nitride and a metal oxynitride, etc., such as silicon oxide, silicon nitride, silicon oxynitride, aluminum oxide, aluminum nitride and aluminum oxynitride. Examples of a fluorine resin include, for example, polytetrafluoroethylene, polyvinylidene fluoride, polychlorotrifluoroethylene, tetrafluoroethylene-perfluoroalkylvinyl ether copolymer, tetrafluoroethylene-hexafluoropropylene copolymer, tetrafluoroethylene-ethylene copolymer, chlorotrifluoroethylene-ethylene copolymer, etc. Silicone resins include organopolysiloxanes (for example, dimethylpolysiloxane, etc.) and their modified (for example, such as polyether-modified, phenol-modified, amine-modified, silanol-modified, trimethylsilyl-modified, carbinol-modified, carboxyl-modified, epoxy-modified, acrylic-modified or methacryl-modified) forms. Such materials may be provided at least on the portions of the inner surface of the container that are to contact the pharmaceutical composition. Such a material is provided on at least a portion of the inner surface of the container. In one embodiment, the material is provided on the entire inner surface of the container. In another embodiment, the container itself is formed of the material. In a preferred embodiment, the container is provided with a film containing the material, on its inner surface. When the container has a film containing the material on its inner surface, the thickness may be not less than 0.1 µm and not more than 0.2 µm, for example. In a more preferred embodiment, the film containing the material is provided on all of the portions of the inner surface of the container that can potentially contact with the pharmaceutical composition.

In a preferred embodiment from the viewpoint of storage stability, for example titer retention rate, the material is selected from the group consisting of silicon oxide, silicon nitride, silicon oxynitride, aluminum oxide, aluminum nitride and aluminum oxynitride. The material is more preferably selected from the group consisting of silicon oxide, silicon nitride and silicon oxynitride, even more preferably silicon oxide and most preferably silicon dioxide.

The film containing the material may be formed by a wet or dry film-forming method known in the prior art. Wet film-forming methods include coating methods, for example. The film containing the material is preferably formed by, for example, a dry film-forming method such as chemical vapor deposition (CVD), physical vapor deposition, spray pyrolysis deposition or sputtering, and more preferably it is formed by CVD or spray pyrolysis deposition. From the viewpoint of maintaining storage stability, for example titer retention rate, it is more preferably formed by CVD, with plasma chemical vapor deposition (plasma CVD) being more preferred.

Examples of the container include, but are not limited to, for example, a container provided with a film containing a material selected from the group consisting of silicon oxide, silicon nitride and silicon oxynitride on the inner surface, where the film is formed by CVD, a container provided with a film containing silicon dioxide on the inner surface, where the film is formed by CVD, a container provided with a film containing a material selected from the group consisting of silicon oxide, silicon nitride and silicon oxynitride on the inner surface, where the film is formed by plasma CVD, and a container provided with a film containing silicon dioxide on the inner surface, where the film is formed by plasma CVD.

The container provided with a film containing such a material on the inner surface may be a commercially available silica-coated vial, silicone-coated vial or fluorine resin-coated vial, etc.

It is considered that providing the inner surface of the container with such a material as described above can, for example, potentially reduce contamination of foreign matter such as metal ions from the base material of the container into the pharmaceutical composition. It is considered that reducing contamination of foreign matter may potentially be related to an effect of suppressing reduction in the enzyme activity according to the present invention. However, this presumed mechanism is not in any way restrictive on the technical scope of the present invention.

The water content of the lyophilized preparation may be not more than 5% (w/w), for example, preferably not more than 3% (w/w), and more preferably not more than 2% (w/w). The "water content," as used herein, is the value measured by a coulometric titration method.

In one embodiment, the amount of saccharide-degrading enzyme contained per container may be less than 10 μg, for example. The amount of saccharide-degrading enzyme contained per container may be set in a numerical range consisting of combinations of any numerical values from among less than 0.1 μg, 0.5 μg, 1 μg, 2 μg, 2.5 μg, 4 μg, 5 μg, 6 μg, 7 μg, 8 μg, 9 μg, 9.5 μg, 9.8 μg and 10 μg. Specifically, the amount of saccharide-degrading enzyme contained per container may be not less than 0.1 μg, not less than 0.5 μg, not less than 1 μg, not less than 2 μg, not less than 2.5 μg, or not less than 4 μg, and not more than 5 μg, not more than 6 μm, not more than 7 μg, not more than 9.5 μg, or not more than 9.8 μg. In a preferred embodiment, the amount of saccharide-degrading enzyme contained per container is not less than 0.1 μg and not more than 9.8 μg. In a more preferred embodiment, the amount of saccharide-degrading enzyme contained per container is not less than 2 μg and not more than 7 μg. In a particularly preferred embodiment, the amount of saccharide-degrading enzyme contained per container is not less than 2.5 μg and not more than 5 μg.

The term "titer" means the enzyme activity (units) per 1 μg of saccharide-degrading enzyme, and it is expressed in a unit of unit/μg. In one embodiment, the titer of the lyophilized saccharide-degrading enzyme is not less than 0.3 (unit/μg). In another embodiment, the titer of the lyophilized saccharide-degrading enzyme is not less than 0.3 (unit/μg) and not more than 1 (unit/μg). In another embodiment, the titer of the lyophilized saccharide-degrading enzyme is not less than 0.32 (unit/μg) and not more than 1 (unit/μg). In another embodiment, the titer of the lyophilized saccharide-degrading enzyme is not less than 0.33 (unit/μg) and not more than 1 (unit/μg). In another embodiment, the titer of the lyophilized saccharide-degrading enzyme is not less than 0.36 (unit/μg) and not more than 1 (unit/μg).

In one embodiment, the titer of the lyophilized saccharide-degrading enzyme is not less than 0.3 (unit/μg) and not more than 0.5 (unit/μg). In another embodiment, the titer of the lyophilized saccharide-degrading enzyme is not less than 0.33 (unit/μg) and not more than 0.5 (unit/μg), or not less than 0.36 (unit/μg) and not more than 0.5 (unit/μg).

The "unit (U)" indicates the activity of the saccharide-degrading enzyme, with 1 unit being the amount that frees the equivalent of 1 micromole of decomposition product from substrate per unit time, under optimum temperature and optimum pH conditions. For example, when the saccharide-degrading enzyme is chondroitinase ABC, 1 unit is the amount that frees 1 micromole of the unsaturated disaccharide per minute from sodium chondroitin sulfate (sodium chondroitin sulfate ester conforming to the Japanese Pharmaceutical Codex 2002), under conditions of pH 8.0, 37° C.

In one embodiment, the titer of a saccharide-degrading enzyme is preferably such that the saccharide-degrading enzyme in the pharmaceutical composition contained in the container in an amount necessary for a single dose is not less than 75%, and more preferably not less than 80%, where 100% is defined as the titer before putting into the container.

In one embodiment, the enzyme activity (saccharide-degrading enzyme activity) per container may be less than 5 units, for example. In another embodiment, the enzyme activity per container may be not more than 4.5 units, for example. In another embodiment, the enzyme activity per container may be not more than 4.1 units, for example. In another embodiment, the enzyme activity per container may be not more than 4 units, for example. In another embodiment, the enzyme activity per container is not less than 0.1 unit and not more than 4.5 units, for example. In another embodiment, the enzyme activity per container is not less than 0.1 unit and not more than 4.1 units, for example. In another embodiment, the enzyme activity per container is not less than 0.1 unit and not more than 4 units, for example. In another embodiment, the enzyme activity per container is not less than 0.9 units and not more than 2.5 units, not less than 0.9 units and not more than 2 units, not less than 1.25 units and not more than 2 units, or 1.5 units.

According to one embodiment of the present invention, it is possible to provide a package having a storage stability for a duration of 12 months or longer. In a preferred embodiment, the package has a storage stability for a duration of 24 months or longer, and in a more preferred embodiment, the package has a storage stability for a duration of 36 months or longer. Although the upper limit for the storage stability is not particularly restricted, it may be 48 months or shorter, or 36 months or shorter, for example.

Here, the phrase "has a storage stability" means that the titer (%) after standing storage in a sealed and light-shielded state under prescribed conditions (for example, 12 months or longer at 5° C.±3° C., 6 months or longer at 25° C.±2° C., or 3 months or longer or 6 months or longer at 40° C.±2° C.) is maintained at a pharmaceutically acceptable level. The "storage stability" herein is evaluated as the titer retention rate (%), for example. For example, the titer retention rate after storage of the sample for 12 months or longer at 5° C.±3° C. is, for example, not less than 90%, and preferably not less than 95%. The titer retention rate after storage of the sample for 24 months or longer at 5° C.±3° C. is, for example, not less than 90%, and preferably not less than 95%. The titer retention rate after storage of the sample for 36 months or longer at 5° C.±3° C. is, for example, not less than 90%, and preferably not less than 95%. The titer retention rate after storage of the sample for 6 months or longer at 25° C.±2° C. is, for example, not less than 90%, and preferably not less than 95%. The titer retention rate after storage of the sample for 3 months or longer at 40° C.±2° C. is, for example, not less than 90%, and preferably not less than 95%. The titer retention rate after storage of the sample for 6 months or longer at 40° C.±2° C. is, for example, not less than 65%, preferably not less than 70%, and more preferably not less than 75%. The term "titer retention rate (%)" means the value of the titer (%) after storage of the package of the present invention under conditions with a prescribed temperature (for example, 5° C.±3° C., 25° C.±3° C. or 40° C.±2° C.), calculated against 100% as the titer at the start of storage. A value of 100% means that the enzyme activity is the same at and after the start of storage.

According to one embodiment of the present invention, it is possible to provide a package having a shelf life of 12 months or longer. In a preferred embodiment, the package has a shelf life of 24 months or longer, and in a more preferred embodiment, the package has a shelf life of 36 months or longer. Although the upper limit for the shelf life is not particularly restricted, it may be 48 months or shorter, or 36 months or shorter, for example.

As used herein, the "shelf life" means the period during which a drug can be expected to exhibit the same efficacy from the time when the drug has been confirmed to exhibit that efficacy, after subsequent storage by a specific storage method (for example, being sealed and light-shielded at 5° C.±3° C., sealed and light-shielded at 25° C.±2° C., or sealed and light-shielded at 40° C.±2° C.).

The use of the pharmaceutical composition as described herein may be selected from among various known uses for saccharide-degrading enzymes. For example, examples of uses of pharmaceutical compositions containing saccharide-degrading enzymes as active ingredients can include, but are not particularly limited to, treatment for hernia, lysosomal disease, keloids, hypertrophic scars, muscular dystrophy and spinal cord injury. In a preferred embodiment, the pharmaceutical composition is used for treatment of hernia. In a more preferred embodiment, it is used for treatment of disc herniation (for example, lumbar disc herniation).

As used herein, "treatment" includes not only complete curing, but also amelioration of all or some of the symptoms of a disease, and suppression (including maintenance and slowed progression) of progression or prevention of a disease. Here, prevention includes preventing onset of symptoms associated with a disease, when the symptoms are not being exhibited. Prevention also includes, for example, preventing onset of organic lesions or suppressing development of symptoms not yet manifested, when symptoms associated with a disease are present even if no clear organic lesions are apparent.

The terms "as an active ingredient" and "effective dose," as used herein, mean an amount of ingredient suited for a reasonable risk/benefit ratio, and sufficient to obtain the desired response without excessive harmful side-effects (toxicity, irritation, etc.). The terms "as an active ingredient" and "effective dose" may vary depending on various factors such as the symptoms, physical constitution, age and sex of the patient to be treated. However, a person skilled in the art can determine the effective dose based on the results of one or more specific test examples in combination with common general technical knowledge, without having to conduct a separate test for each combination of the various factors.

As used herein, "patient" means an animal, and preferably a mammal (for example, a human, mouse, rat, hamster, guinea pig, rabbit, dog, cat, horse, etc.), and more preferably a human.

In a preferred embodiment, the pharmaceutical composition contained in the container is provided in a sterile state. There are no particular restrictions on the sterilization method for the pharmaceutical composition, and sterilization may be performed in any method known in the prior art, such as filtration sterilization or dry heat sterilization.

The form of administration of the pharmaceutical composition is also not particularly restricted and may be selected as appropriate for the disease to be treated, the symptoms, the severity, the patient attributes (for example, age, etc.), etc. The lyophilized preparation may be used as a solution in any desired solvent (for example, water for injection, physiological saline, etc.). The form of administration may be any route of administration, for example, such as intradiscal injection, intravenous injection, intramuscular injection, hypodermic injection or drip infusion. The dose of the pharmaceutical composition can also be appropriately set by a person skilled in the art according to the disease to be treated, the symptoms, the severity, the patient attributes (for example, age, etc.), etc.

Preferred specific modes of the present invention will now be described by way of example, with the understanding that they are not intended to limit the technical scope of the present invention. A pharmaceutical composition for treatment disc herniation may be explained as an example, as follows. But it is natural that the use of pharmaceutical compositions may not be limited.

(Package 1)
  Active ingredient: Chondroitinase ABC
  Material provided on inner surface of the container: Silicon dioxide
  Amount of active ingredient per container: not less than 2.5 µg and less than 10 µg
  Enzyme titer: not less than 0.32 (unit/µg) and not more than 1 (unit/µg)
  Enzyme activity per container: not less than 0.4 units and not more than 4.5 units
  Application: Disc herniation (Package 2)
  Active ingredient: Chondroitinase ABC
  Material provided on inner surface of the container: Silicone resin
  Amount of active ingredient per container: not less than 2.5 µg and less than 10 µg
  Enzyme titer: not less than 0.32 (unit/µg) and not more than 1 (unit/µg)
  Enzyme activity per container: not less than 0.4 units and not more than 4.5 units
  Application: Disc herniation (Package 3)
  Active ingredient: Chondroitinase ABC
  Material provided on inner surface of the container: Fluorine resin
  Amount of active ingredient per container: not less than 2.5 µg and less than 10 µg
  Enzyme titer: not less than 0.32 (unit/µg) and not more than 1 (unit/µg)
  Enzyme activity per container: not less than 1 unit and not more than 4.5 units
  Application: Disc herniation (Package 4)
  Active ingredient: Chondroitinase ABC
  Material provided on inner surface of the container: At least one selected from among silicon dioxide, silicone resin and fluorine resin
  Amount of active ingredient per container: not less than 2 µg and not more than 5 µg
  Enzyme titer: not less than 0.32 (unit/µg) and not more than 0.5 (unit/µg)
  Enzyme activity per container: not less than 1.25 units and not more than 2.5 units
  Application: Disc herniation (Package 5)
  Active ingredient: Chondroitinase ABC
  Material provided on inner surface of the container: At least one selected from among silicon dioxide, silicone resin and fluorine resin Amount of active ingredient per container: not less than 2.5 μg and not more than 5 μg
Enzyme titer: not less than 0.32 (unit/μg) and not more than 0.5 (unit/μg)
Enzyme activity per container: 1.5 units
Application: Disc herniation (2) Kit In one embodiment, there is provided a kit containing a package, and a package insert or label explaining the use of the pharmaceutical composition for treatment of hernia, lysosomal disease, keloids, hypertrophic scars, muscular dystrophy or spinal cord injury.

It is sufficient that the kit contains a package comprising the pharmaceutical composition contained in a container, and a package insert or label explaining the use of the pharmaceutical composition for treatment of hernia, lysosomal disease, keloids, hypertrophic scars, muscular dystrophy or spinal cord injury. In other words, it may also contain other constituent components.

(3) Production Method

One aspect of the present invention relates to a method for producing a package comprising a pharmaceutical composition and a container containing the pharmaceutical composition, the production method including a first step of putting a solution containing a saccharide-degrading enzyme into a container comprising at least one material selected from the group consisting of fine ceramics, silicone resins and fluorine resins on its inner surface, and a second step of lyophilizing the solution to obtain a pharmaceutical composition.

In the first step, although the solvent used for preparation of the solution containing the saccharide-degrading enzyme is not particularly restricted, for example, a buffer solution such as water, physiological saline or phosphate buffer may be used. The solution may also include a pharmaceutically acceptable carrier as mentioned above. Although the pH of the solution containing the saccharide-degrading enzyme contained in the container is not particularly restricted, it is preferably in the range of 6.5 or higher and 7.5 or lower.

In one embodiment, the solution containing the saccharide-degrading enzyme is contained in the container in the first step such that the enzyme activity per container is less than 5 units. In another embodiment, the solution containing the saccharide-degrading enzyme is contained in the container in the first step such that the enzyme activity per container is not more than 4.5 units. In another embodiment, the solution containing the saccharide-degrading enzyme is contained in the container in the first step such that the enzyme activity per container is not more than 4.1 units. In another embodiment, the solution containing the saccharide-degrading enzyme is contained in the container in the first step such that the enzyme activity per container is not less than 0.5 units and not more than 4.5 units. In another embodiment, the solution containing the saccharide-degrading enzyme is contained in the container in the first step such that the enzyme activity per container is not less than 0.5 units and not more than 4.1 units. In a preferred embodiment, the solution containing the saccharide-degrading enzyme is contained in the container in the first step such that the enzyme activity per container is not more than 4 units. In a more preferred embodiment, the solution is contained in the container such that the enzyme activity per container is not less than 0.5 units and not more than 4 units. In another embodiment, the solution is contained in the container such that the enzyme activity per container is not less than 0.5 units and not more than 3.5 units, not less than 1.1 units and not more than 3 units, not less than 1 unit and not more than 2 units, not less than 1.25 units and not more than 1.6 units, or 1.5 units.

The second step includes a lyophilization step in which the solution containing the saccharide-degrading enzyme is frozen and the moisture is removed by sublimation while in a frozen state for drying. In the second step, drying is carried out until the water content of the pharmaceutical composition after lyophilization becomes not more than 5% (w/w), for example. The drying in the second step is preferably carried out until the water content of the pharmaceutical composition after lyophilization becomes not more than 3% (w/w), and more preferably the drying is carried out until the water content becomes not more than 2% (w/w).

The production method according to the present invention can directly employ the descriptions, examples, preferred ranges, etc., for the above-described "(1) composition and package" and the above-described "(2) kit."

As another mode, the present invention also includes the use of a pharmaceutical composition and a container in production of a package to be used for treatment of hernia, lysosomal disease, keloids, hypertrophic scars, muscular dystrophy or spinal cord injury, wherein the pharmaceutical composition is a lyophilized preparation containing at least one enzyme from among saccharide-degrading enzymes and matrix metalloproteases as an active ingredient, and the container comprises at least one material selected from the group consisting of fine ceramics, silicone resins and fluorine resins on its inner surface. Also, as another mode, the present invention also includes the use of a package for treatment of hernia, lysosomal disease, keloids, hypertrophic scars, muscular dystrophy or spinal cord injury, wherein the package comprises a pharmaceutical composition which is a lyophilized preparation containing at least one enzyme from among saccharide-degrading enzymes and matrix metalloproteases as an active ingredient, contained in a container which comprises at least one material selected from the group consisting of fine ceramics, silicone resins and fluorine resins on its inner surface. Further, as another mode, the present invention also includes a package to be used for treatment of hernia, lysosomal disease, keloids, hypertrophic scars, muscular dystrophy or spinal cord injury, wherein the package comprises a pharmaceutical composition which is a lyophilized preparation containing at least one enzyme from among saccharide-degrading enzymes and matrix metalloproteases as an active ingredient, contained in a container which comprises at least one material selected from the group consisting of fine ceramics, silicone resins and fluorine resins on its inner surface.

Exemplary embodiments of the present invention will now be described, with the understanding that the present invention is not limited by these embodiments.

<1> A package comprising a pharmaceutical composition and a container, wherein the pharmaceutical composition is a lyophilized preparation containing at least one enzyme from among saccharide-degrading enzymes and matrix metalloproteases as an active ingredient, the container contains the pharmaceutical composition, and the inner surface of the container comprises at least one material selected from the group consisting of fine ceramics, silicone resins and fluorine resins.

<2> The package according to <1>, wherein the material is selected from the group consisting of silicon oxide, silicon nitride, silicon oxynitride, aluminum oxide, aluminum nitride and aluminum oxynitride.

<3> The package according to <2>, wherein the silicon oxide is silicon dioxide.

<4> The package according to any one of <1> to <3>, wherein the container comprises a film containing the material, on its inner surface.

<5> The package according to <4>, wherein the film containing the material is formed by chemical vapor deposition, physical vapor deposition, spray pyrolysis deposition or sputtering.

<6> The package according to <5>, wherein the chemical vapor deposition is plasma chemical vapor deposition.

<7> The package according to any one of <1> to <6>, wherein an amount of enzyme contained per container is less than 10 μg.

<8> The package according to any one of <1> to <7>, wherein a titer of the enzyme is not less than 0.3 (unit/μg).

<9> The package according to any one of <1> to <8>, wherein an enzyme activity per container is less than 5 units.

<10> The package according to any one of <1> to <9>, wherein the enzyme activity of the enzyme is not less than 75%, where 100% is defined as the value before lyophilization.

<11> The package according to any one of <1> to <10>, wherein the package has a storage stability for the duration of not less than 12 months at 5° C.±3° C.

<12> The package according to any one of <1> to <11>, wherein the enzyme is a glycosaminoglycan degrading enzyme.

<13> The package according to <12>, wherein the glycosaminoglycan degrading enzyme is a chondroitinase.

<14> The package according to <13>, wherein the chondroitinase is chondroitinase ABC.

<15> The package according to any one of <1> to <14>, wherein the matrix metalloprotease is matrix metalloprotease 7.

<16> The package according to any one of <1> to <15>, wherein the pharmaceutical composition includes a pharmaceutically acceptable carrier.

<17> The package according to <16>, wherein the carrier includes at least one of polyalkylene glycol and sucrose.

<18> The package according to any one of <1> to <17>, wherein the pharmaceutical composition is for treatment of disc herniation, lysosomal disease, keloids, hypertrophic scars, muscular dystrophy or spinal cord injury.

<19> The package according to any one of <1> to <18>, wherein the container is a vial, syringe or ampule.

<20> A pharmaceutical composition obtained by lyophilizing a solution containing at least one enzyme from among saccharide-degrading enzymes and matrix metalloproteases, in a container comprising at least one material selected from the group consisting of fine ceramics, silicone resins and fluorine resins on its inner surface.

<21> The pharmaceutical composition according to <20>, wherein a titer of the enzyme is not less than 0.3 unit/μg.

<22> The pharmaceutical composition according to <20> or <21>, wherein the pharmaceutical composition is a unit dose formulation having an amount of enzyme of less than 10 μg.

<23> The pharmaceutical composition according to any one of <20> to <22>, wherein an enzyme activity is less than 5 units.

<24> The pharmaceutical composition according to any one of <20> to <23>, wherein the composition has a storage stability for a duration of not less than 12 months at 5° C.±3° C.

<25> The pharmaceutical composition according to any one of <20> to <24>, wherein the enzyme is a glycosaminoglycan degrading enzyme.

<26> The pharmaceutical composition according to <25>, wherein the glycosaminoglycan degrading enzyme is a chondroitinase.

<27> The pharmaceutical composition according to <26>, wherein the chondroitinase is chondroitinase ABC.

<28> The pharmaceutical composition according to any one of <20> to <27>, wherein the matrix metalloprotease is matrix metalloprotease 7.

<29> The pharmaceutical composition according to any one of <20> to <28>, wherein the pharmaceutical composition includes a pharmaceutically acceptable carrier.

<30> The pharmaceutical composition according to <29>, wherein the carrier includes at least one of polyalkylene glycol and sucrose.

<31> The pharmaceutical composition according to any one of <20> to <30>, wherein the pharmaceutical composition is for treatment of hernia, lysosomal disease, keloids, hypertrophic scars, muscular dystrophy or spinal cord injury.

<32> A kit containing a package according to any one of <1> to <19>, and a package insert or label explaining the use of the pharmaceutical composition for treatment of hernia, lysosomal disease, keloids, hypertrophic scars, muscular dystrophy or spinal cord injury.

<33> A method for producing a package comprising a pharmaceutical composition and a container containing the pharmaceutical composition, the production method including a step of putting a solution containing at least one enzyme from among saccharide-degrading enzymes and matrix metalloproteases into a container comprising at least one material selected from the group consisting of fine ceramics, silicone resins and fluorine resins on its inner surface, and a step of lyophilizing the solution to obtain a pharmaceutical composition.

<34> The production method according to <33>, wherein the material is selected from the group consisting of silicon oxide, silicon nitride, silicon oxynitride, aluminum oxide, aluminum nitride and aluminum oxynitride.

<35> The production method according to <34>, wherein the silicon oxide is silicon dioxide.

<36> The production method according to any one of <33> to <35>, wherein the inner surface of the container comprises a film containing the material.

<37> The production method according to <36>, wherein the film containing the material is formed by chemical vapor deposition, physical vapor deposition, spray pyrolysis deposition or sputtering.

<38> The production method according to <37>, wherein the chemical vapor deposition is plasma chemical vapor deposition.

<39> The production method according to any one of <33> to <38>, wherein an amount of enzyme contained is less than 10 μg.

<40> The method according to any one of <33> to <39>, wherein a titer of the enzyme in the pharmaceutical composition is not less than 0.3 (unit/μg).

<41> The production method according to any one of <33> to <40>, wherein an enzyme activity of the solution contained in the container is less than 5 units.
<42> The production method according to any one of <33> to <41>, wherein the enzyme activity of the enzyme after lyophilization is not less than 75%, where 100% is defined as the enzyme activity before lyophilization.
<43> The production method according to any one of <33> to <42>, wherein the enzyme is a glycosaminoglycan degrading enzyme.
<44> The production method according to <43>, wherein the glycosaminoglycan degrading enzyme is a chondroitinase.
<45> The production method according to <44>, wherein the chondroitinase is chondroitinase ABC.
<46> The production method according to any one of <33> to <45>, wherein the matrix metalloprotease is matrix metalloprotease 7.
<47> The production method according to any one of <33> to <46>, wherein the pharmaceutical composition includes a pharmaceutically acceptable carrier.
<48> The production method according to <47>, wherein the carrier includes at least one of polyalkylene glycol and sucrose.
<49> The production method according to any one of <33> to <48>, wherein the pharmaceutical composition is for treatment of hernia, lysosomal disease, keloids, hypertrophic scars, muscular dystrophy or spinal cord injury.
<50> The production method according to any one of <33> to <49>, wherein the container is a vial, syringe or ampule.

EXAMPLES

The present invention will now be described in greater detail. However, this description is not intended to restrict the technical scope of the present invention.

Preparation Example 1

1) Preparation of Chondroitinase ABC

Chondroitinase ABC was prepared according to the method described in Japanese Published Unexamined Patent Application No. H6-153947. That is, it was produced by purification from a *Proteus vulgaris* culture supernatant. The titer of the obtained chondroitinase ABC was 0.40 U/μg.

2) Enzyme Activity Measurement and Concentration Measurement of Chondroitinase ABC The enzyme activity of the chondroitinase ABC was measured by the following method.

The enzyme sample (chondroitinase ABC) was diluted 4000-times with 0.01% (w/v) casein reagent (20 mM phosphate buffer). To 100 μL of the diluted enzyme sample, there was added and mixed 400 μL of substrate solution (3 mg/ml chondroitin sulfate sodium ester (Japanese Pharmaceutical Codex), 50 mM 2-amino-2-hydroxymethyl-1,3-propanediol, 50 mM sodium acetate, pH 8). After reacting the solution at 37° C. for 20 minutes, it was heated for 1 minute in a water bath at 100° C. The reaction mixture was cooled to room temperature, and 5.0 mL of 0.05 M hydrochloric acid was added to prepare a sample solution. Standard chondroitinase ABC was diluted 400-times with 0.01% (w/v) casein reagent. The same procedure for preparation of the sample solution was carried out with 100 μL of the diluted standard chondroitinase ABC solution, to prepare a standard solution. The same procedure for preparation of the sample solution was also carried out for 100 μL of 0.01% (w/v) casein reagent, to prepare a control solution. The absorbance $A_T$, $A_S$ and $A_B$ at a wavelength of 232 nm were measured for the sample solution, standard solution and control solution, using ultraviolet-visible spectrophotometry, and the enzyme solution activity (U/mL) of each was determined by the following formula. Here, the enzyme solution activity is the enzyme activity per unit liquid volume.

Enzyme solution activity (U/mL)=$(A_T-A_B)/(A_S-A_S) \times 4000/400 \times Us$ $A_T$: Absorbance of sample solution
$A_B$: Absorbance of control solution
$A_S$: Absorbance of standard solution
Us: Enzyme solution activity of standard chondroitinase ABC (U/mL)

1 U (unit) was defined as the value of enzyme activity that catalyzes reaction to free 1 micromole of unsaturated disaccharide in 1 minute, under the reaction conditions specified above. The values for the enzyme activity used herein were determined based on the enzyme solution activity.

The amount of chondroitinase ABC enzyme (protein, μg) was measured by the Lowry method. That is, 2.5 mL of alkaline copper reagent was added to and mixed with 0.5 mL of the enzyme sample (chondroitinase ABC) diluted 50-times with pure water, and the mixture was allowed to stand for 10 minutes at room temperature (20° C. or higher and 25° C. or lower). Next, 0.25 mL of 1 mol/L phenol reagent was added to the liquid and allowed to stand for 30 minutes at room temperature to prepare a sample solution. Bovine serum albumin was dissolved in water to prepare a solution to a concentration of 30 μg/mL, 40 μg/mL, 50 μg/mL, 60 μg/mL or 70 μg/mL, and the same procedure for the 50-times diluted enzyme sample was carried out for 0.5 mL of each solution to prepare a standard solution. The same procedure for the 50-times diluted enzyme sample was also carried out for 0.5 mL of water, to prepare a blank solution. The absorbance of each solution at a wavelength of 750 nm was measured. The absorbance and protein concentration of the standard solution was plotted by a linear regression method, to determine a standard curve most closely approximating each point. The amount of protein in each sample solution was determined from the obtained standard curve and the absorbance of the sample solution.

3) Preparation of Buffer for Enzyme Solution

A buffer for enzyme solution was prepared so as to have the following composition.

(Composition; per 1 L of distilled water for injection)
Sodium hydrogenphosphate (sodium hydrogenphosphate dodecahydrate): 1.125 mg
Sodium dihydrogen phosphate: 0.3 mg
Sucrose: 5 mg
Polyethylene glycol 3350: 10 mg
pH: 6.5 or higher and 7.5 or lower

REFERENCE EXAMPLE

The above-described enzyme sample (chondroitinase ABC) was dissolved in the buffer for enzyme solution. The obtained enzyme solution was filled into glass vials (vial 3010; product of Fuji Glass Co., Ltd.) so as to have the following enzyme amounts, respectively:
Sample 1: 15.0 μg/vial (6.0 U/vial)
Sample 2: 30.0 μg/vial (12.0 U/vial)
Sample 3: 60.0 μg/vial (24.0 U/vial)

The enzyme solution contained in each vial was lyophilized (to a water content of not more than 2% (w/w) after lyophilization). After lyophilization, the pressure inside the vial was recovered with nitrogen gas and sealed with a rubber stopper to obtain a package.

Each sample was measured for enzyme activity (U/vial) after lyophilization (n=3). The titer (U/μg) after lyophilization of the enzyme was calculated based on the obtained value for the enzyme activity. The results are shown in Table 1. The titer is the enzyme activity per amount of enzyme.

TABLE 1

|  | Sample 1 | Sample 2 | Sample 3 |
|---|---|---|---|
| Enzyme amount (μg/vial) | 15.0 | 30.0 | 60.0 |
| Enzyme activity before lyophilization (U/vial) | 6.0 | 12.0 | 24.0 |
| Enzyme activity after lyophilization (U/vial) | 4.6 | 10.5 | 21.8 |
| Titer after lyophilization (U/μg) | 0.307 | 0.350 | 0.363 |

As shown in Table 1, a smaller amount of enzyme contained in the vial resulted in lower titer.

Example 1

A chondroitinase ABC solution prepared by using buffer for enzyme solution was filled into a 3 mL glass vial so as to have 9.1 μg enzyme/vial (3.63 U/vial; Sample 4 to Sample 6) or 1.3 μg enzyme/vial (0.50 U/vial; Sample 7). The glass vials used were vial 3010 (product of Fuji Glass Co., Ltd.; Sample 4), vial 3010 silicoat (having a silicon dioxide coating formed by spray pyrolysis deposition (SPD) on the inner surface of the vial; product of Fuji Glass Co., Ltd.; Sample 5) and SCHOTT® Type I Plus (having a silicon dioxide coating formed by plasma impulse chemical vapor deposition (PICVD) on the inner surface of the vial; product of Schott AG, Sample 6, Sample 7).

The enzyme solution contained in each vial was lyophilized (to a water content of not more than 2% (w/w) after lyophilization). After drying, the pressure inside the vial was recovered with nitrogen gas and it was sealed with a rubber stopper to obtain a package containing a unit dose.

Each sample was measured for enzyme activity (U/vial) after lyophilization (n=10). The titer (U/μg) after lyophilization of the enzyme was calculated based on the obtained value for the enzyme activity. The results are shown in Table 2.

TABLE 2

|  | Sample 4 | Sample 5 | Sample 6 | Sample 7 |
|---|---|---|---|---|
| Enzyme amount (μg/vial) | 9.1 | 9.1 | 9.1 | 1.3 |
| Enzyme activity before lyophilization (U/vial) | 3.63 | 3.63 | 3.63 | 0.50 |
| Enzyme activity after lyophilization (U/vial) | 2.60 | 2.99 | 3.13 | 0.43 |
| Titer after lyophilization (U/μg) | 0.286 | 0.328 | 0.344 | 0.331 |

Example 2

After rolling up the packages of Sample 4 and Sample 6 with aluminum caps, they were subjected to dry heat sterilization at 250° C. for 5 hours. The enzyme activities after dry heat sterilization were 2.53 U/vial for Sample 4 and 3.12 U/vial for Sample 6.

Example 3

The enzyme solution was filled into a vial 3010 (product of Fuji Glass Co., Ltd.; Sample 8) and SCHOTT® Type I Plus (product of Schott AG; Sample 9) and lyophilized (to a water content of not more than 2% (w/w)). After lyophilization, the pressure inside the vial was recovered with nitrogen gas and sealed with a rubber stopper to obtain a package. The obtained package was stored by standing for 1 month, 3 months or 6 months under conditions of 40±2° C. with light shielded, and the titer after each storage period was determined (n=3). Table 3 shows the results of calculating the titer retention rate (%) after each storage period, where 100% was defined as the titer at the start of storage.

TABLE 3

|  | Titer retention rate (%) | | |
|---|---|---|---|
|  | 1 month | 3 months | 6 months |
| Sample 8 | 94 | 92 | 65 |
| Sample 9 | 95 | 96 | 76 |

Upon storage of Sample 9 by standing for 12 months under conditions of 5° C.±3° C. with light shielded, the titer retention rate was 98%.

Preparation Example 2

1) Preparation of Chondroitinase ABC

Chondroitinase ABC was prepared according to the method described in Japanese Published Unexamined Patent Application No. H6-153947, in the same manner as Preparation Example 1. The titer of the obtained chondroitinase ABC was 0.42 U/μg.

Example 4

Buffer for enzyme solution was added to the chondroitinase ABC obtained in Preparation Example 2 to prepare an enzyme solution. The enzyme solution was filled into the glass vial so as to have 9.8 μg enzyme/vial (4.1 U/vial; Sample 10 to Sample 12). The glass vials used were SCHOTT® Type I Plus (having a silicon dioxide coating formed by plasma impulse chemical vapor deposition (PICVD) on the inner surface of the vial; product of Schott AG, Sample 10), a silicone-coated vial (having a silicone resin film on the inner surface of the vial; product of Iwata Glass Industrial Co., Ltd.; Sample 11), and a fluorine-coated vial (having a polytetrafluoroethylene film on the inner surface of the vial; product of Universal Co., Ltd.; Sample 12).

The enzyme solution contained in each vial was lyophilized (to a water content of not more than 2% (w/w) after lyophilization). After drying, the pressure inside the vial was recovered with nitrogen gas and it was sealed with a rubber stopper to obtain a package containing a unit dose.

Each sample was measured for enzyme activity (U/vial) after lyophilization (n=3). The titer (U/μg) after lyophilization of the enzyme was calculated based on the obtained value for the enzyme activity. The results are shown in Table 4.

TABLE 4

|  | Sample 10 | Sample 11 | Sample 12 |
| --- | --- | --- | --- |
| Enzyme amount (μg/vial) | 9.8 | 9.8 | 9.8 |
| Enzyme activity before lyophilization (U/vial) | 4.10 | 4.10 | 4.10 |
| Enzyme activity after lyophilization (U/vial) | 4.05 | 4.06 | 3.86 |
| Titer after lyophilization (U/μg) | 0.415 | 0.416 | 0.395 |

Although the present invention has been described in relation to specific examples and various embodiments, it will be readily appreciated by a person skilled in the art that numerous modifications and applications of the embodiments described herein are possible without departing from the spirit and scope of the present invention.

The present application claims the priority to Japanese Patent Application No. 2018-35884 which was filed in the Japan Patent Office on Feb. 28, 2018 and Japanese Patent Application No. 2018-141542 which was filed in the Japan Patent Office on Jul. 27, 2018, and the entirety of their content is incorporated in the present application by reference. All literatures, patent applications, and technical standards described herein are incorporated herein by reference to the same extent as if individual literatures, patent applications, and technical standards are specifically and individually indicated to be incorporated by reference.

The invention claimed is:

1. A package comprising
a pharmaceutical composition and a container,
wherein the pharmaceutical composition is a lyophilized preparation containing a saccharide-degrading enzyme as an active ingredient,
wherein the container contains the pharmaceutical composition and has at least one material selected from the group consisting of fine ceramics, silicone resins and fluorine resins at an inner surface of the container,
wherein the saccharide-degrading enzyme is chondroitinase ABC, and
wherein an amount of the enzyme in the container is less than 10 μg.

2. The package according to claim 1, wherein an enzyme activity per the container is less than 5 units.

3. The package according to claim 1, wherein the enzyme has a titer of not less than 0.3 unit/μg.

4. The package according to claim 1, wherein the package has a storage stability for a duration of not less than 12 months at 5° C.±3° C.

5. A method for producing a pharmaceutical composition contained in a container, the method comprising:
putting a solution comprising a saccharide-degrading enzyme into the container having at least one material selected from the group consisting of fine ceramics, silicone resins and fluorine resins on its inner surface, and
lyophilizing the solution,
wherein the saccharide-degrading enzyme is chondroitinase ABC, and
wherein an amount of the enzyme in the container is less than 10 μg.

6. The method according to claim 5, wherein a titer of the enzyme in the pharmaceutical composition is not less than 0.3 unit/μg.

7. The method according to claim 5, wherein an enzyme activity of the solution to be put into the container is less than 5 units.

8. A pharmaceutical composition obtained by lyophilizing a solution comprising a saccharide-degrading enzyme in a container which has at least one material selected from the group consisting of fine ceramics, silicone resins and fluorine resins at an inner surface of the container,
wherein the saccharide-degrading enzyme is chondroitinase ABC, and
wherein an amount of the enzyme in the container is less than 10 μg.

9. The package according to claim 1, wherein an enzyme activity per the container is less than 5 units.

10. The package according to claim 1, wherein the enzyme has a titer of not less than 0.3 unit/μg.

11. The package according to claim 2, wherein the enzyme has a titer of not less than 0.3 unit/μg.

12. The package according to claim 1, wherein the package has a storage stability for a duration of not less than 12 months at 5° C.±3° C.

13. The package according to claim 2, wherein the package has a storage stability for a duration of not less than 12 months at 5° C.±3° C.

14. The package according to claim 3, wherein the package has a storage stability for a duration of not less than 12 months at 5° C.±3° C.

15. The method according to claim 6, wherein an enzyme activity of the solution to be put into the container is less than 5 units.

* * * * *

UNITED STATES PATENT AND TRADEMARK OFFICE
CERTIFICATE OF CORRECTION

| | | |
|---|---|---|
| PATENT NO. | : 12,090,228 B2 | Page 1 of 1 |
| APPLICATION NO. | : 16/975252 | |
| DATED | : September 17, 2024 | |
| INVENTOR(S) | : Mine Higuchi | |

It is certified that error appears in the above-identified patent and that said Letters Patent is hereby corrected as shown below:

In the Specification

Column 2, Line 54, please change, "(PNGaseF," to -- (PNGase F, --.

In the Claims

Column 16, Line 12 and Line 13, please change, "$(A_T-A_B)/(A_S-A_S)$" to -- $(A_T-A_B)/(A_S-A_B)$ --.

Signed and Sealed this
Seventeenth Day of December, 2024

Derrick Brent
*Acting Director of the United States Patent and Trademark Office*